United States Patent [19]

Lapidus et al.

[11] Patent Number: 6,143,529

[45] Date of Patent: Nov. 7, 2000

[54] METHODS FOR IMPROVING SENSITIVITY AND SPECIFICITY OF SCREENING ASSAYS

[75] Inventors: Stanley N. Lapidus, Bedford, N.H.; Anthony P. Shuber, Milford, Mass.

[73] Assignee: Exact Laboratories, Inc., Maynard, Mass.

[21] Appl. No.: 09/277,016

[22] Filed: Mar. 26, 1999

Related U.S. Application Data

[63] Continuation-in-part of application No. 08/876,857, Jun. 16, 1997, Pat. No. 5,928,870, which is a continuation-in-part of application No. 08/700,583, Aug. 14, 1996, Pat. No. 5,670,325.

[51] Int. Cl.[7] .............................. C12P 19/34; C12Q 1/68; G01N 33/574; G01N 33/00; C07H 21/02

[52] U.S. Cl. ........................... 435/91.2; 435/6; 435/91.1; 435/7.23; 436/94; 536/23.1

[58] Field of Search ............................... 435/6, 7.23, 91.1, 435/91.2, 183; 436/63, 64, 94; 536/23.1, 24.3, 24.33, 25.41, 25.3

[56] References Cited

PUBLICATIONS

Mulcahy et al., A prospective study of K–ras mutations in the plasma of pancreatic cancer patients. Clin. Cancer Res. 4, 271–275, Feb. 1998.

Sidransky et al., Identification of ras oncogene mutations in the stool of patients with curable colorectal tumors. Science 256, 102–105, 1992.

*Primary Examiner*—Bradley L. Sisson
*Assistant Examiner*—Frank Lu
*Attorney, Agent, or Firm*—Testa, Hurwitz & Thibeault, LLP

[57] ABSTRACT

Methods of the invention comprise assays for markers indicative of cancer or precancer. Assays of the invention are performed on samples obtained from a patient by non-invasive or minimally-invasive methods. The invention provides nucleic acid indicia of cancer or precancer with high sensitivities and high specificities for detection.

33 Claims, 1 Drawing Sheet

METHODS FOR IMPROVING SENSITIVITY AND SPECIFICITY OF SCREENING ASSAYS

This application is a continuation-in-part of U.S. Ser. No. 08/876,857, filed Jun. 16, 1997, now U.S. Pat. No. 5,928,870 which is a continuation-in-part of U.S. Ser. No. 08/700,583, filed Aug. 14, 1996 (U.S. Pat. No. 5,670,325).

FIELD OF THE INVENTION

The invention relates to assays to detect nucleic acid markers of cancer with high specificity and high sensitivity for detection.

BACKGROUND OF THE INVENTION

Cancer is thought to arise from a multi-step process that typically involves multiple genetic mutations leading to uncontrolled cell growth. Many cancers are curable if detected early in their development. For example, colorectal cancers typically originate in the colonic epithelium, and are not extensively vascularized (and therefore not invasive) during early stages of development. The transition to a highly-vascularized, invasive and ultimately metastatic cancer commonly takes ten years or longer. If the presence of cancer is detected prior to extensive vascularization, surgical removal typically is an effective cure. However, colorectal cancer is often detected only upon manifestation of clinical symptoms, such as pain and bloody stool. Generally, such symptoms are present only when the disease is well established, and often after metastasis has occurred. Similarly, with the exception of the Pap smear for detection of pre-malignant cervical lesions, diagnostic screening methods for other types of cancer are best at detecting established disease.

Most diagnostic assays for cancer are invasive, or at least uncomfortable. Invasive procedures range from performing a tissue biopsy to surgery. Cancer screening procedures frequently result in significant patient discomfort. For example, magnetic resonance imaging requires confinement of the patient, and colonoscopy requires sedation. The discomfort associated with typical invasive screening methods reduces patient compliance with routine screening procedures.

Moreover, screening for the early detection of cancer (i.e., prior to the onset of symptoms and/or metastasis) often results in an intolerable level of false positive and false negative results. The likelihood of a false positive test result is a function of the specificity of the test. The specificity of a test (expressed as a percentage) is the likelihood that any individual who is negative for disease tests negative for that disease. On the other hand, false negative results are a property of the sensitivity of the test. Sensitivity (also expressed as a percentage) provides the likelihood that a test for a specific disease will identify as positive an individual having that disease. Thus, 5% of the individuals determined to have a disease using an assay with a specificity of 95% will actually not have the disease. Similarly, an assay with a sensitivity of 95% will incorrectly identify a diseased individual as disease-free 5% of the time.

The problems of sensitivity and specificity are exaggerated in assays for the early detection of cancer because patient samples on which such early detection is performed typically contain relatively small amounts of cancerous cellular material in relation to non-cancerous cellular material. In many cases, patient samples are a heterogeneous mixture of large amounts of normal cells and small amounts of cancerous cells. A good example of such a heterogeneous sample is stool. The typical stool sample contains cells and cellular debris sloughed from the colonic epithelium, by-products of digestion, and bacteria. In its early stages, colorectal cancer is thought to affect only about 1% of colonic epithelial cells. Any attempt to detect nucleic acids from the 1% of affected cells in the heterogeneous background of the stool sample might give rise to very low sensitivities. Attempts to identify the presence of the indicia of cancer in other heterogeneous samples, such as sputum, pus, urine, nipple aspirate, etc., presents similar problems.

Recently, a number of genetic mutations have been associated with cancer. For example, alterations in the p53 gene, the Kras oncogene, and the apc tumor suppressor gene are thought to be participants in the multi-step pathway leading to cancer. It has been suggested that mutations in those genes might be a basis for molecular screening assays for the early stages of certain types of cancer. See e.g., Sidransky, et al., Science, 256: 102–105 (1992). Attempts have been made to identify and use nucleic acid markers that are indicative of cancer. However, even when such markers are found, using them to screen patient samples, especially heterogeneous samples, has proven unsuccessful either due to an inability to obtain sufficient sample material, or due to the low sensitivity that results from measuring only a single marker. For example, simply obtaining adequate human DNA from one type of heterogeneous sample (stool) has proven difficult. See Villa, et al., Gastroenterol., 110: 1346–1353 (1996) (reporting that only 44.7% of all stool specimens, and only 32.6% of stools from healthy individuals produced sufficient DNA for mutation analysis). Other reports in which adequate DNA has been obtained have reported low sensitivity in identifying a patient's disease status based upon a single cancer-associated mutation. See Eguchi, et al., Cancer, 77: 1707–1710 (1996) (using a p53 mutation as a marker for cancer).

Accordingly, there is a need in the art for high-sensitivity, high-specificity assays for the detection of molecular indicia of cancer, especially in heterogeneous samples.

SUMMARY OF THE INVENTION

Methods of the invention solve the problem of obtaining accurate (high sensitivity and high specificity) results in an assay for indicia of cancer or precancer in a heterogeneous sample.

The present invention provides assays conducted on samples obtained non-invasively or minimally-invasively for cancer or precancer in which the assays have a high sensitivity for detection of cancer or precancer when it is present in a patient sample, and a high specificity against false positive results. In a preferred embodiment, methods of the invention provide the benefits of high sensitivity and high specificity in an assay to detect a small amount of a cancer marker (e.g., a nucleic acid) in a heterogeneous sample having predominantly non-cancerous cells and cellular debris. Accordingly, such methods are especially useful for early detection of cancer or precancer. Methods of the invention greatly increase the accuracy of molecular screening and diagnostic assays for the early detection of cancer or precancer.

The present invention contemplates that one reason prior art non-invasive methods (i.e., methods conducted on samples obtained non-invasively or minimally invasively) for detecting molecular indicia (especially nucleic acid mutations) of cancer have failed to provide satisfactory results is that such methods have not addressed maintaining high specificity and/or high sensitivity in the assay. Such methods also fail to recognize the benefits of combining high sensitivity and high specificity features in an assay to detect early indicia of cancer, especially when the detection is performed in a heterogeneous sample. The present invention recognizes that screening assays for indicia of cancer, especially early-stage cancer (e.g., when cancer indicia represents about 1% of the cells and cellular debris in an appropriate sample as discussed below), are improved by increasing the specificity and/or the sensitivity of the assay. As described below, the specificity and sensitivity of molecular assays can be improved in several ways.

In a preferred embodiment, methods of the invention comprise selecting one or more nucleic acid target(s) that is (are) suspected to be mutated in cancer or precancer, identifying in a biological sample the presence of the one or more selected target(s), such that the probability of identifying as positive any sample comprising target is at least about 44%, and preferably about 50%, and most preferably between about 60% and about 95%, and the probability of identifying as negative a sample not having any target is at least about 85%, and preferably between about 90% and about 100%.

In another preferred embodiment, the present invention provides methods for improving the sensitivity and specificity of molecular cancer screening assays by analyzing a plurality of target nucleic acids suspected to be mutated in cancer or precancer, such that the cumulative sensitivity of analyzing the plurality of targets is at least about 50%, and the cumulative specificity of analyzing the plurality of targets is at least about 85%.

Methods of the invention also comprise selecting nucleic acid mutations for analysis in a cancer or precancer screening assay based upon the probability of occurrence of the mutations in cancer patients, and such that the probability of identifying at least one of the mutations in a patient sample having at least one of the mutations is between about 50% and about 95%. Methods of the invention also comprise selecting one or more nucleic acid mutations in order to optimize the sensitivity and specificity of a cancer or precancer screening assay, and conducting the assay in order to diagnose cancer or precancer. In a preferred embodiment, screening assays of the invention analyze at least two, and preferable between about 3 and about 20 markers (e.g., mutations, loss of heterozygosity, sequence length variations, nucleic acid molecular weight variations, variations in amounts of amplifiable nucleic acid) in patient samples in order to improve the sensitivity and specificity of detection. Such "multiple target" assays allow improved sensitivity because the increased number of markers that are analyzed decreases the likelihood that a patient presenting with indicia of cancer or precancer will be misdiagnosed as negative (i.e., as not having cancer).

Methods of the invention further comprise selecting nucleic acid markers suspected to be indicative of cancer or precancer, validating the informativeness of the markers in order to select a subset of markers that provide high sensitivity and specificity in an assay for the detection of cancer or precancer in patient samples, and screening patient samples for the presence of the selected subset of markers. In a preferred embodiment, the nucleic acid markers are mutations known or suspected to be indicative of cancer or precancer. Also in a preferred embodiment, the validating step comprises determining the extent to which detection of a marker used in connection with a particular screening assay predicts whether a patient from whom the sample was obtained has cancer or precancer. Preferably, such validating methods are performed by comparing results from samples obtained from a first group of patients known to have cancer or precancer and those obtained from a second group known not to have cancer or precancer as determined by an accepted standard (typically invasive) method.

Methods of the invention also comprise combining detection of a mutation known or suspected to be associated with cancer or precancer with detection of loss of heterozygosity at a relevant genomic locus. The combination of analyzing both mutations in cancer-associated nucleic acids, and loss of heterozygosity increases the specificity and sensitivity of any screening assay for cancer or precancer. In a preferred embodiment, such methods comprise validating selected loci for use in a screening assay such that the assay produces results with high sensitivity and high specificity. In a preferred embodiment, the sensitivity of the assay is at least 50%, and the specificity of the assay is at least 85%.

Methods of the invention comprise combining two or more assays for molecular indicia of cancer or precancer in order to achieve a desired level of informativeness. For example, in a preferred embodiment, methods of the invention comprise combining two or more assays selected from quantitative PCR, multiple mutation analysis, detection of loss of heterozygosity, and hybrid capture of one or more mutant nucleic acid markers. Accordingly, increased sensitivity and specificity is observed when an assay based upon the amount of amplifiable DNA is combined with an assay for a particular cancer-associated mutation. Examples of these "combination assays", and their resulting sensitivities and specificities, are provided in the detailed description. Such methods are especially useful when applied to a heterogeneous sample in which the nucleic acid to be detected is present in a very small amount relative to other nucleic acids (as well as other molecules) in the sample.

Methods of the invention also make use of the "informativeness" of markers used therein. The Informativeness of a nucleic acid marker relates to the likelihood of finding the marker in a positive sample. Thus, if a particular mutation, for example a mutation in codon 12 of K-ras, has an informativeness for cancer of 56%, this means that 56% of positive patient samples (i.e., those taken from patients who have cancer) have the K-ras mutation. Methods of the invention combine the use of informative markers (e.g., mutations) and high sensitivity/specificity assays in order to provide reliable screening assays for early diagnosis of cancer or precancer, especially in heterogeneous samples.

For purposes of the present invention a mutation is a deletion, addition, substitution, rearrangement, or translocation in a nucleic acid. A loss of heterozygosity is a form of mutation in which all or a portion of one allele is deleted. Also for purposes of the present invention, the terms "markers", "targets", and "mutations" include nucleic acid (especially DNA) mutations (substitutions, additions, rearrangements, translocations, deletions, etc.), as well as other nucleic acid indicia useful in methods of the invention. Such indicia include the amount of amplifiable nucleic acid in a sample, the length of nucleic acids in a sample, the ratio of long nucleic acids (greater than about 200 bp) to short nucleic acids (less than about 200 bp), and any other nucleic acid variations that differ in patients with cancer and disease-free patients. Also for purposes of the present invention, the terms "healthy" or "disease-free" are intended to mean a patient who does not have cancer or precancer.

Stool is a good example of a heterogeneous sample in which methods of the invention are especially useful. A typical stool sample contains patient nucleic acids, but also contains heterologous nucleic acids, proteins, and other cellular debris consistent with the lytic function of the various nucleases, proteinases, etc. found in the colon. As stool proceeds from the proximal colon to the distal colon, it (under normal circumstances) solidifies. As the solidifying stool passes through the colon, colonic epithelial cells are sloughed onto the stool. If a patient has a developing tumor or adenoma, cells from the tumor or adenoma will also be sloughed onto stool, and they (or their debris) will contain molecular indicia of disease (e.g., mutations or loss of heterozygosity). In the early stages of development, nucleic acid indicative of an adenoma or tumor comprise only about 1% of the nucleic acid in a voided stool. If a patient is left untreated, proportionately more disease-related nucleic acids are found in stool over time. Methods of the invention are useful for detecting early-stage lesions in heterogeneous samples such as stool. Methods of the invention result in a high degree of sensitivity and specificity for the detection of early-stage disease. Methods of the invention are especially useful in detecting, for example, adenomas in the colon. Adenomas are non-metastatic lesions that frequently have the potential for metastasis. If all adenomas in a patient are detected and removed, the probability of complete cure is virtually certain.

In a preferred embodiment, nucleic acids or nucleic acid mutations having a high degree of informativeness are chosen. One or more assay(s) is (are) conducted to reliably detect one or more informative nucleic acids, and a diagnosis is made based upon the presence in a patient sample of any one of the informative nucleic acids. In a preferred embodiment, nucleic acids are chosen as targets for analysis in methods of the invention based upon their length and/or sequence characteristics. For example, it has now been discovered that the quantity and/or length of nucleic acids in stool (a prototypical heterogeneous sample) presents a high degree of informativeness regarding a patient's disease status. Patients having, for example, an adenoma produce stool specimens containing more and longer DNA than specimens produced by healthy patients. Moreover, a number of highly-informative DNA mutations are useful in methods of the invention. These include, mutations in the oncogene, Kras (especially mutations at codons 12 and 13); mutations in the cell-cycle regulator, p53; mutations in the apc gene; mutations in the bat-26 segment of the MSH2 mismatch repair gene; and loss of heterozygosity (typically indicated by massive loss of DNA in one allele but not the other). Finally, methods of the invention provide that the informativeness of an assay is increased by screening multiple mutations simultaneously or in sequence, or by combining different assays.

In another preferred embodiment, methods of the invention provide informative molecular assays for cancer or precancer by providing samples for analysis that have sufficient amplifiable nucleic acid. Thus, in one embodiment, methods of the invention comprise screening samples for amplifiable DNA; classifying samples based upon the amount of DNA capable of being amplified from them; and further screening samples with a predetermined threshold of amplified or amplifiable DNA for the presence of a mutation indicative of cancer or precancer.

In another preferred embodiment, methods of the invention comprise selecting one or more mutational events that are indicative of cancer or precancer, such that the combined informativeness of the one or more events meets or exceeds a predetermined or desired level of informativeness. The informativeness of any mutation or combination of mutations may be validated by an accepted invasive screening technique. For example, in methods to detect colorectal cancer, the informativeness of a molecular assay may be determined by identification of a lesion using colonoscopy.

A detailed description of certain preferred embodiments of the invention is provided below. Other embodiments of the invention are apparent upon review of the detailed description that follows.

DETAILED DESCRIPTION OF THE DRAWINGS

Figure 1:
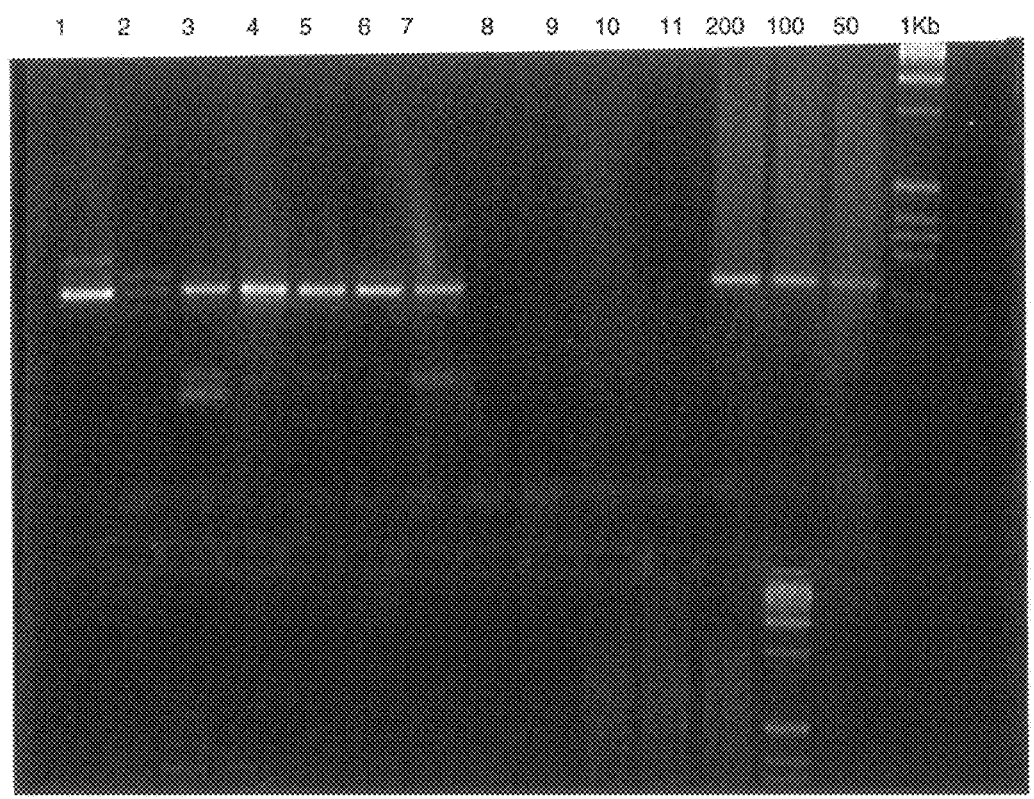

FIG. 1 is a polyacrylamide gel showing exemplary "A", "B", "C", and "F" amplifications for use in assays to determine an amount of amplifiable nucleic acid in a sample. Lanes 1, 4, 5, 6, and 7 show an "A" amplification, lane 2 shows a "C" application, lane 3 shows a "B" amplification, and lane 8 shows an "F" amplification (no amplifiable DNA).

DETAILED DESCRIPTION OF THE INVENTION

Methods of the invention provide non-invasive or minimally-invasive assays for the detection of cancer or precancer at early stages of disease. Methods of the invention are especially useful in detecting cancer or precancer in heterogeneous biological samples. Preferred methods comprise identifying in a patient sample one or more nucleic acid mutations(s) that provide high sensitivity and high specificity for detection of the indicia of cancer or precancer. Methods of the invention may comprise identifying mutations having a known informativeness for cancer or precancer, or may be based upon validating selected mutations or assays to detect them with respect to a standard assay for cancer. By utilizing cancer or precancer markers having a high sensitivity/specificity for detecting the presence of cancer or precancer, methods of the invention provide improvements in non-invasive or minimally-invasive molecular screening assays. For purposes of the present invention, non-invasive or minimally-invasive means that specimens for analysis are obtained either from bodily excretions (e.g. stool, pus, sputum) or bodily fluids such as blood aspirate, or lymph.

The invention will be exemplified with experiments to detect the presence of indicia of colorectal cancer or precancer in samples prepared from patient stool specimens. However, the skilled artisan recognizes that methods of the invention can be practiced using a variety of different samples in order to detect a variety of cancers.

A reason that detection of colorectal cancer or precancer (e.g., an adenoma) is exemplified is that a stool specimen is a good example of a heterogeneous environment in which methods of the invention are especially useful (see above). Moreover, colonoscopy (and sigmoidoscopy, a related technique) is a well-known invasive standard that has a high sensitivity and high specificity (although high cost and low patient compliance) with which methods of the invention can be compared and validated.

Methods of the invention comprise screening a sample, such as one prepared from a stool specimen, for the presence of one or more marker(s) of cancer or precancer (e.g., a colorectal tumor or adenoma), such that the sensitivity of detection is between about 50% and about 100%, and the specificity of detection is between about 85% and about 100%. In a preferred embodiment, methods of the invention combine different types of assays in order to achieve an overall increase in sensitivity and specificity. Thus, methods of the invention comprise conducting an assay for a mutation known to be associated with cancer or precancer, and an assay for a quantity and/or length of DNA expected to occur in cancer or precancer in order to obtain the combined benefits of the sensitivity and specificity of both assays. Moreover, embedded within the concept of utilizing multiple nucleic acid analyses to detect cancer or precancer is the use of multiple genomic targets in each assay in order to provide further increases in sensitivity and specificity. However, as shown below, a single-marker assay is sufficient for practice of the invention if its sensitivity and specificity are within the ranges taught herein.

The genomic targets and assay methods used according to the invention can vary depending upon the desired level of sensitivity and specificity, as well as the type of cancer or precancer the detection of which is desired. Genomic targets (e.g., mutations) are selected based upon their known sensitivity or specificity or by determining a baseline sensitivity and specificity. In preferred embodiments, methods of the invention comprise the detection of a mutation at a single, informative locus. In other embodiments, assays for informative loci are combined in order to achieve improved sensitivity and specificity of detection relative to invasive techniques. Accordingly, methods of the invention contemplate a combination of assays selected from multiple mutation detection, quantitative polymerase chain reaction (i.e., to determine the amount of amplifiable DNA in a sample), sequence-specific hybrid capture, oligo-ligation, amplification refractory mutation system, single-stranded conformational polymorphism detection, sequencing, mismatch detection, and single base extension. Target loci include chromosomes 1, 5, 8,17, and 18, particularly chromosome 5q, chromosome 17p, chromosome 8p, chromosome 1q, and chromosome 18q. Preferred loci for use in methods of the invention include p53, apc, bat-26, and others suspected to be predictive of cancer or precancer.

Other genes are known to be associated with colorectal cancer, and their sensitivity and specificity are determined when not known in the literature by determining the percentage of tumors bearing the mutation, and the percentage of healthy specimens that bear the mutation from a sufficiently large and diverse population. This can be done empirically, or mathematically using algorithms that predict the likelihood of false positive and false negative screening results based upon data relating the presence of a mutation to the presence of cancer or precancer. Confirmation of a patient's clinical status can be accomplished by a standard test such as colonoscopy in the case of colorectal cancer (which has a typical sensitivity of 95% and a typical specificity of 100%).

For the analysis of stool samples, preferred methods of the invention comprise obtaining at least a cross-section or circumfrential portion of a voided stool as taught in U.S. Pat. No. 5,741,650, and co-pending, co-owned U.S. patent application Ser. No. 09/059,718, both of which are incorporated by reference herein. While a cross-sectional or circumfrential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA). However, as taught in co-pending, co-owned U.S. patent application Ser. No. 60/122,177, incorporated by reference herein, it has been discovered that the use of at least 150 mM EDTA greatly improves the yield of nucleic acid from stool. Thus, a preferred buffer for stool homogenization comprises phosphate buffered saline, 20–100 mM NaCl or KCl, at least 150 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed.

Nucleic acids to be analyzed are chosen based upon known or suspected relationships between specific mutations and cancer or precancer. If desired, sequence-specific hybrid capture is used to isolate specific nucleic acids from the sample. Target nucleic acids may be analyzed by any method of the art. Examples of preferred methods include enumerative analysis of the loss of heterozygosity as taught in U.S. Pat. No. 5,670,325, incorporated by reference herein. Enumerative methods do not require knowledge of the sequence of a mutant nucleic acid. Rather such methods determine that there has been an alteration (deletion, substitution, addition, rearrangement, or other mutation) in a wild-type nucleic acid. The investigated loci are chosen based upon the likelihood of an alteration being associated with cancer or precancer. Enumerative methods compare the number in a sample of a wild-type nucleic acid known not to be altered in cancer or precancer with the number of a wild-type nucleic acid known or suspected to be altered in cancer or precancer. A statistically-significant difference in the two numbers indicates a positive screen.

Mutations in target nucleic acids may also be measured by single base extension techniques to identify a single nucleotide variant indicative of cancer or precancer. Preferably, single base extension assay are cycled as taught in co-owned, co-pending U.S. patent application Ser. No. 09/067,212, incorporated by reference herein. Briefly, cycled single base extension reactions comprise annealing a nucleic acid primer immediately 5' to a region containing a single base to be detected. The single base to be detected represents a marker for mutation. The mutation may be a single point mutation or may be a larger mutation for which the single base is a marker. Two separate reactions are conducted. In the first reaction, primer is annealed to target, and labeled (preferably $^{32}P$) nucleic acids complementary to non-wild type (e.g. mutants indicative of disease) variants at the single base to be detected, and unlabeled dideoxy nucleic acids complementary to the wild-type base are combined. Primer extension is stopped the first time a wild-type (dideoxy) base is added to the primer. Presence of label in the extended primer is indicative of the presence of a mutation. A second tube, the positive control contains labeled nucleic acid complementary to the wild-type base in the presence of the primer. A DNA polymerase, such as SequenaseTM (Amersham), is used for primer extension. In a preferred embodiment, a thermostable polymerase, such as Taq or thermal sequenase is used to allow more efficient cycling. Once an extension reaction is completed, the first and second probes bound to target nucleic acids are dissociated by heating the reaction mixture above the melting temperature of the hybrids. The reaction mixture is then cooled below the melting temperature of the hybrids and additional primer is permitted to associate with target nucleic acids for another round of extension reactions. In a preferred embodiment, 10 to 50 cycles of extension reactions are conducted. In a most preferred embodiment, 30 cycles of extension reactions are conducted. After completion of all cycles, extension products are isolated and detected. In alternative embodiments, chain-terminating methods other than dideoxy nucleotides may be used. For example, chain termination occurs when no additional bases are available for incorporation at the next available nucleotide on the primer.

Methods of the invention are also useful for screening populations of patients in order to identify characteristics in population samples that are indicative of cancer or adenoma. For example, methods of the invention comprise high sensitivity, high specificity screening of populations of patients in order to correlate nucleic acid mutations present in a subset of patient samples with the presence of disease in those patients. Thus, methods of the invention comprise detecting genomic variations in patient samples, correlating those variations with confirmed disease, and using the variations associated with confirmed disease as a diagnostic screen for the disease in subsequent patient samples. Such methods preferably are performed on pooled samples, such as stool samples, from identified populations of patients (e.g., diseased, healthy). Such methods are preferably based upon variations in single nucleotide polymorphic loci. The sensitivity and specificity of detecting variants in those loci as a function of disease is determined. Those loci that predict disease at predefined levels of sensitivity and specificity are selected for use in screening assays for unknown patient samples.

The following examples provide specific exemplification of the concepts discussed above. The examples utilize a subset of mutational events that are shown to be predictive of disease. Other mutations are contemplated to function as high sensitivity, high specificity diagnostic or screening markers in assays of the invention. Moreover, the assays exemplified below are for purposes of illustration. The invention contemplates a variety of assays useful to screen patient samples for cancer or precancer as long as the assays provide a predetermined level of sensitivity and specificity of at least about 44% and at least about 85%, respectively.

EXAMPLE 1

Multiplex Screening of Stool Samples

An experiment was conducted to determine the effects of multiple mutation analysis alone on the sensitivity and specificity of cancer or precancer detection in the stool specimens described above. Fifteen mutations, all known or suspected to occur in colorectal cancer or precancer were used to screen the 40 patient samples. The following table catalogs the mutations that were assayed.

TABLE 1

| Gene | Mutation |
| --- | --- |
| Kras, codon 13 | Position 2, G to A |
| Kras, codon 12 | Position 1, G to A |
| Kras, codon 12 | Position 2, G to A |
| Apc, codon 1450 | Position 1, C to T |
| Apc, codon 1378 | Position 1, C to T |
| Apc, codon 1367 | Position 1, C to T |
| Apc, codon 1309 | Deletion of 5 base pairs |
| P53, codon 175 | Position 2, G to tA |
| P53, codon 273 | Position 1, C to T |
| P53, codon 273 | Position 2, G to A |
| P53, codon 282 | Position 1, C to T |
| P53, codon 245 | Position 1, G to A |
| P53, codon 245 | Position 2, G to A |
| P53, codon 248 | Position 1, C to T |
| P53, codon 248 | Position 2, G to A |

According to methods of the invention, multiple mutation analysis is a preferred means for increasing the sensitivity and specificity of cancer or precancer detection. For example, there are cumulative benefits of combining the informativeness (see above) of a mutation at one allele (e.g., Kras, codon 13, position 2) with the informativeness of a second allele (e.g., Kras codon 12, position 1, or apc codon 1450, position 1) in order to increase the overall sensitivity and specificity of the assay. Accordingly, the benefits of one aspect of the invention are presented below.

Stool specimens were collected from 40 individuals who presented at the Mayo Clinic (Rochester, Minn.) with symptoms or history indicating that a colonoscopy should be performed. Each stool sample was frozen. Immediately after providing a stool sample, all individuals were given a colonoscopy in order to determine their disease status. Colonoscopy, an invasive test requiring sedation of the patient, has a sensitivity approaching 95%, and a specificity of nearly 100% for the diagnosis of colonic neoplasia. Based upon the colonoscopy results and subsequent histological analysis of biopsy samples taken during colonoscopy, individuals were placed into one of three groups: normal, cancer, and adenoma. An adenoma, or polyp, is considered clinically relevant if it has a diameter of 1 cm or greater. Thus, all individuals in the adenoma group had a polyp of at least 1 cm in diameter. Patients in the cancer group had tumors diagnosed as cancer, and the disease-free individuals were those for whom colonoscopy showed no sign of cancer or adenoma. Based upon the colonoscopy results, 21 patients were diagnosed with cancer, 9 patients were diagnosed with an adenoma greater than 1 cm, and 10 patients were free of cancer or adenoma.

Multiple mutation analysis was then performed, on a blinded basis (i.e., scientists performing the assays did not know the results of colonoscopy or histology), on each sample. Each frozen stool specimen, weighing from 7-33 grams, was thawed, homogenized in 500 mM Tris, 16 mM EDTA, and 10 mM NaCl, pH 9.0, at a volume to mass ratio of about 3:1. Samples were then rehomogenized in the same buffer to a final volume-to-mass ratio of 20: 1, and spun in glass macro beads at 2356×g. The supernatant was collected and treated with SDS and proteinase k. The DNA was then phenol-chloroform extracted and precipitated with alcohol. The precipitate was suspended in 10 mM Tris and 1 mM EDTA (1×TE), pH 7.4. Finally, the DNA was treated with Rnase.

Human DNA was isolated from the precipitate by sequence-specific hybrid capture. Biotinylated probes against portions of the p53, K-ras, and apc genes were used. The K-ras probe was 5'GTGGAGTATTTGATAGTGTATTAACCT-TATGTGTGAC 3' (SEQ ID NO: 1). There were two apc probes: apc-1309 was 5'TTCCAGCAGTGTCACAGCACCCTAGAAC-CAAATCCAG 3' (SEQ ID NO: 2), and apc-1378 was 5'CAGATAGCCCTGGACAAACMTGCCACG-MGCAGAAG 3' (SEQ ID NO: 3). There were four probes against p53, the first (hybridizing to a portion of exon 5) was 5'TACTCCCCTGCCCTCAACAAGAT-GTTTTGCCMCTGG3' (SEQ ID NO:4), the second (hybridizing to a portion of exon 7) was 5'ATTTCTTCCATACTACTACCCATCGACCTCTCATC3' (SEQ ID NO: 5), the third, also hybridizing to a portion of exon 7 was 5'ATGAGGCCAGTGCGCCTTGGGGAGACCT-GTGGCAAGC3' (SEQ ID NO: 6); and finally, a probe against exon 8 had the sequence 5'GAAAGGACAAGGGTGGTTGGGAGTA-GATGGAGCCTGG3' (SEQ ID NO: 7). A 10 ul aliquot of each probe (20 pmol/capture) was added to a suspension containing 300 ul DNA in the presence of 310 ul 6M GITC buffer for 2 hours at room temperature. Hybrid complexes were isolated using streptavidin-coated beads (Dynal). After washing, probe-bead complexes were suspended at 25° C. for 1 hour in 0.1×TE buffer, pH7.4. The suspension was then heated for 4 minutes at 85° C., and the beads were removed.

Captured DNA was then amplified using PCR, essentially as described in U.S. Pat. No. 4,683,202, incorporated by reference herein. Seven separate PCRs were run in duplicate using primers directed against Kras, apc, and p53. The primers listed below were used:

| | | |
|---|---|---|
| PCR-A FOR kras | 5'GCG GTC CCA AAA GGG TCA GTC CTG CTG AAA ATG ACT GAA 3' (SEQ ID NO: 8) | 39 |
| PCR-A-REV | 5'(Biotin)GCG GTC CCA AAA GGG TCA GTC ATG AAA ATG GTC AGA GAA A 3'(SEQ ID NO: 9) | 40 |
| PCR-B-FOR APC-1309 | 5'GCG GTC GCT TTT GGG TCA GTT GTA GTT CAT TAT CAT CTT T 3' (SEQ ID NO: 10) | 40 |
| PCR-B-REV | 5'(Biotin)GCG GTC GCT TTT GGG TCA GTC TTC GCT CAC AGG ATC TTC A 3'(SEQ ID NO: 11) | 40 |
| PCR-C-FOR APC-1378 | 5'GCG GTC GCA AAA GGG ACA GTA GGC ACA AAG CTG TTG AAT 3' (SEQ ID NO: 12) | 39 |
| PCR-C-REV | 5'(Biotin)GCG GTC GCA AAA GGG ACA GTT ATC AAG TGA ACT GAC AGA A 3'(SEQ ID NO: 13) | 41 |
| PCR-D-FOR APC-1450 | 5'GCG GTC CCA AAA GGG TCA GTC ACC TCC ACC ACC TCC TCA A 3' (SEQ ID NO: 14) | 40 |
| PCR-D-REV | 5'(Biotin)GCG GTC CCA AAA GGG TCA GTG TAT CAG CAT CTG GAA GAA 3'(SEQ ID NO: 15) | 39 |
| PCR-E-FOR p53 Exon 5 | 5'GCG GTC CCA AAA GGG TCA GTC CAT CTA CAA GCA GTC A 3'(SEQ ID NO: 16) | 37 |
| PCR-E-REV | 5'(Biotin)GCG GTC CCA AAA GGG TCA GTC AGA CCT AAG AGC AAT CA 3'(SEQ ID NO: 17) | 38 |
| PCR-F-FOR p53 Exon 7 | 5'GCG GTC CCA AAA GGG TCA GAT ACC ACC ATC CAC TAC AA 3'(SEQ ID NO: 18) | 38 |
| PCR-F-REV | 5'(Biotin)GCG GTC CCA AAA GGG TCA GAG TAT GGA AGA AAT CGG TAA 3'(SEQ ID NO: 19) | 39 |
| PCR-G-FOR p53 Exon 8 | 5'GCG GTC CCT TTT GGG TCA CTC TGC CTC TTG CTT CTC TTT T 3' (SEQ ID NQ: 20) | 40 |
| PCR-G-REV | 5'(Biotin)GCG GTC CCT TTT GGG TCA CTC TTG TCC TGC TTG CTT ACC T 3'(SEQ ID NO: 21) | 40 |

Samples were heated to 94° C. for 5 minutes, and then 40 cycles were conducted between 94° C., 60° C., and 72° C. (1 minute each), followed by one cycle at 72° C. for 5 minutes.

The presence of the 15 mutations listed in Table 1 above was determined by cycling single base extension (cycling SBE), essentially as described above and in co-pending, co-owned U.S. patent application Ser. No. 09/067,212, incorporated by reference herein. Briefly, two reactions were run. In the first reaction, primer was hybridized adjacent the single base to be detected. $^{32}$P labeled nucleotide complementary to the expected mutant base and unlabeled dideoxy nucleotide complementary to the wild-type base were added. Primer was extended, and the presence of labeled product indicated a mutation was present in the sample. A second reaction was run as a positive control in which only labeled wild-type complement was added to the reaction mixture. Primer extension incorporating the labeled base assured that the reaction was running properly.

Primers used in SBE were as follows:

| Name | Site | Codon/Position | Sequence | |
|---|---|---|---|---|
| SBE-A1 | Kras | k12p.1 | 5'AAC TTG TGG TAG TTG GAG CT 3' | (SEQ ID NO: 22) |
| SBE-A2 | Kras | k12p.2 | 5'ACT TGT GGT AGT TGG AGC TG 3' | (SEQ ID NO: 23) |
| SBE-A3 | Kras | k13p.2 | 5'TGT GGT AGT TGG AGC TGG TG 3' | (SEQ ID NO: 24) |
| SBE-B1 | APC-1309 | 1309(_5) | 5'AAA TAG CAG AAA TAA AA 3' | (SEQ ID NO: 25) |
| SBE-C1 | APC-1378 | 1367 | 5'CTC CCT CCA AAA GTG GTG CT 3' | (SEQ ID NO: 26) |
| SBE-C2 | APC-1378 | 1378 | 5'GTC CAC CTG TAC ACT ATG TT 3' | (SEQ ID NO: 27) |
| SBE-D1 | APC-1450 | 1450 | 5'CTC AAA CAG CAC AAA CCA AG 3' | (SEQ ID NO: 28) |
| SBE-E1 | p53 Exon 5 | 175p.2 | 5'CAT GAC GGA GGT TGT GAG GC 3' | (SEQ ID NO: 29) |
| SBE-F1 | p53 Exon 7 | 245p.1 | 5'GTA ACA GTT CCT GCA TGG GC 3' | (SEQ ID NO: 30) |
| SBE-F2 | p53 Exon 7 | 245p.2 | 5'TAA CAG TTC CTG CAT GGG CG 3' | (SEQ ID NO: 31) |
| SBE-F3 | p53 Exon 7 | 248p.1 | 5'CCT GCA TGG GCG GCA TGA AC 3' | (SEQ ID NO: 32) |
| SBE-F4 | p53 Exon 7 | 248p.2 | 5'CTG CAT GGG CGG CAT GAA CC 3' | (SEQ ID NO: 33) |
| SBE-G1 | p53 Exon 8 | 273p.1 | 5'GAC GGA ACA GCT TTG AGG TG 3' | (SEQ ID NO: 34) |
| SBE-G2 | p53 Exon 8 | 273p.2 | 5'ACG GAA CAG CTT TGA GGT GC 3' | (SEQ ID NO: 35) |
| SBE-G3 | p53 Exon 8 | 282p.1 | 5'GTG CCT ATC CTG GGA GAG AC 3' | (SEQ ID NO: 36) |

Reactions were performed under standard denaturation, annealing, extension cycling for 30 cycles and visualized on a 15% denaturing polyacrylamide gel. Counts per minute (CPM) from each cycling reaction were entered into a Packard Instant Imager (wire chamber counter). Percent allele heterogeneity was determined as:

$$\frac{cpm\ mutant/cpm\ wild\ type}{cmp\ 1\%\ mutant\ ctrl/cpm\ 1\%\ wild\text{-}type\ ctrl}$$

A positive sample was defined as one in which at least one of the two replicates possessed a mutation with 1% heterogeneity for at least one of the single bases that was analyzed. Any sample in which at least one of the genes analyzed showed a mutation in duplicate was considered positive. The results are summarized below in Table 2. The total numbers of patients in the cancer/adenoma and normal groups are shown under the column "patient status".

TABLE 2

| Patient Status | Lesions Detected By Colonoscopy | Lesions Detected By SBE | Sensitivity of SBE | Specificity of SBE |
|---|---|---|---|---|
| Cancer/Adenoma (30) | 21/9 | 11/4 | 52%/44% | 100%/100% |
| Normal (10) | 0 | 0 | | |

As shown in Table 2, multiple mutation analysis using SBE correctly identified 11 out of 21 cancerous lesions identified by colonoscopy for a sensitivity of 52%. Multiple mutation analysis revealed 4 out of 9 adenomas for a sensitivity of 44%. In both cases, multiple mutation analysis using SBE correctly identified all disease-free individuals, resulting in no false positives (specificity of 100%).

A fecal occult blood test, was run in parallel with the SBE test on all samples from patients diagnosed with an adenoma. Fecal occult blood testing failed to diagnosis any of the 9 adenoma-positive samples, and thus had a sensitivity of 0%. Accordingly, multiple mutation analysis has a far greater sensitivity and specificity than the most common non-invasive technique currently available (fecal occult blood).

EXAMPLE 2

Quantitative DNA Analysis

In this experiment, the same 40 samples described in Example 1 were independently analyzed for their overall content of DNA in order to determine if the amount of amplifiable DNA in stools produced by individuals with cancer or precancer was different than the amount of amplifiable DNA produced in stools from cancer-free individuals. Samples were analyzed "blind", and later correlated to colonoscopy results as described below.

Aliquots of the DNA obtained from the 40 patients described above in Example 1 were amplified using the primers described above. Each sample was amplified through 7 loci in duplicate (for a total of 14 amplifications for each locus). The products of PCR were placed on a 4% Nusieve (FMC Biochemical) gel (3% Nusieve, 1% agarose), and stained with ethidium bromide (0.5 ug/ml). The resulting amplified DNA was graded based upon the relative intensity of the stained gels. An "A" amplification produced the greatest cumulative intensity (and hence the greatest amount of DNA) after 40 cycles of PCR, "B" and "C" amplifications produced proportionately less gel intensity; and "F" amplifications produced no or little intensity. FIG. 1 shows exemplary A, B, C, and F amplifications. There is sufficient reproducibility in PCR to allow the skilled artisan to classify an amount of amplifiable nucleic acid based upon standards for healthy and cancer populations, or based upon inspection of the gel photograph in FIG. 1. The assay only requires that one differentiate "A" amplifications from any of "B", "C", and "F" amplifications. An "A" amplification is one that has a band intensity of that in lane 1 of FIG. 1, or to another gel band of similar intensity (e.g., lanes 4, 5, 6, or 7 of FIG. 1). The markers to the right of FIG. 1 show exemplary amounts of DNA giving rise to A, B, and C amplifications. Thus 200 pg of DNA (lane 12 in the Figure) results in an "A" amplification, and 100 pg (lane 13 in the Figure) results in a "B" amplification, and 50 pg (lane 14 in the Figure) results in a "C" amplification.

Any DNA sample that produced 9 "A" amplifications out of a possible 14 was graded as positive for cancer or adenoma. The results are shown in Table 3 below:

TABLE 3

| Patient Status | Number of Patients Determined By Colonscopy | Number of Patients Determined By Quantitative DNA Analysis ("A" Amps) | Sensitivity of Quantitative DNA Analysis | Specificity of Quantitative DNA Analysis |
|---|---|---|---|---|
| Cancer/Adenoma (30) | 21/9 | 14/5 | 67%/56% | 100%/100% |
| Cancer-free (10) | 0 | 0 | | |

As shown in Table 3, the amount of amplifiable DNA in stool is highly predictive of a patient's disease status. These results are consistent with the idea that patients with cancer or adenoma in the colon slough more cells (and therefore more DNA) onto the forming stool. Moreover, The DNA derived from cancer or adenoma cells is more intact than DNA derived from normal cells since cancer and adenoma cells have avoided apoptotic degradation of DNA.

EXAMPLE 3

Combined Multiple Mutation and Quantitative Analysis

The results obtained in Examples 1 and 2 above were combined to determine if further increases in sensitivity and specificity would be observed.

A positive sample in this experiment was one which produced an "A" amplification, and produced a positive multiple mutation result (under the criteria described in Example 1). Samples were prepared and analyzed on a "blind" basis (i.e., without knowing colonoscopy results a priori) as described above. The results are shown in Table 4 below:

TABLE 4

| Patient Status | Number of Patients Diagnosed By Colonscopy | Number of Patients Diagnosed By a Combination of Quant. And Multiple Mutation | Sensitivity | Specificity |
|---|---|---|---|---|
| Cancer/Adenoma | 21/9 | 16/7 | 76%/78% | 100%/100% |

The results of the combined quantitative and multiple mutation analyses show a sensitivity of detection of 76% for cancer, and 78% for adenomas, each having a specificity of 100%. These results far exceed those of other non-invasive or minimally-invasive techniques (e.g., fecal occult blood testing which has a sensitivity of 0).

EXAMPLE 4

Diagnostic Assay Using Bat-26

The Bat-26 mismatch repair locus (shown in SEQ ID NO: 37) was next used to assess the same 40 samples described above. Deletions in Bat-26 have been associated with colorectal cancer or adenomas. Samples were prepared as described above. A primer was hybridized to the portion of the Bat-26 locus immediately upstream of the poly-A tract. Unlabeled deoxy thymidine, a mixture of labeled and unlabeled deoxycytosine, and unlabeled dideoxy adenine were added along with polymerase. The primer was extended through the poly-A region. The labeled and unlabelled cytosine was extended for the next three bases (nucleotides 222–224, all guanines in the intact sequence) such that label was incorporated into each extended primer. After the poly-A tract and the three guanines, there exist two thymidines in the intact sequence. Thus, the dideoxy adenosine stops primer extension by addition at the end of a primer that has been extended through the poly-A and triguanine regions. Strands were separated, and the length of the strands was observed on a polyacrylamide gel to detect deletions in the poly-A tract. The results are presented below in Table 5:

TABLE 5

| Patient Status | Diagnosis By Colonoscopy | Diagnosis By Bat-26 Detection | Sensitivity of Bat-26 Detection | Specificity of Bat-26 Detection |
|---|---|---|---|---|
| Cancer/Adenoma | 21/9 | 4/0 | 19%/0% | 100%/0% |

As shown above, Bat-26 alone did not provide the high sensitivity achieved using multiple mutation or quantitation alone, but showed high sensitivity in comparison with other single locus detection assays. Moreover, as shown below, Bat-26 in combination with the other techniques described above produced an overall increase in sensitivity and specificity.

EXAMPLE 5

Cumulative Effects of Kras, Multiple Mutation, Quantitation, and BAT-26

The results obtained above for Kras, multiple mutation analysis, quantitation, and Bat-26 were combined to determine the cumulative effects of using combinations of those techniques in order to produce increased sensitivity and specificity in a non-invasive assay for cancer or precancer. The results are summarized below in Table 6:

TABLE 6

| Assay Combination | Kras and Quantitation and BAT-26 | Quantitation and BAT-26 | Multiple Mutation and Quantitation and BAT-26 |
|---|---|---|---|
| Sensitivity for Detection of Cancer/Adenoma | 80%/56% | 80%/56% | 90%/78% |
| Specificity for Detection of Cancer/Adenoma | 100% | 100% | 100% |

As shown in the summary above, the combination of multiple mutation analysis, quantitative PCR, and Bat-26 produced a sensitivity approaching that of colonoscopy. A combination of multiple mutation analysis and quantitation alone also produces very high sensitivities. All assays resulted in a specificity of 100% (no false positive results), which is comparable to colonoscopy.

The foregoing experiments show that even a single high-sensitivity/high specificity non-invasive or minimally-invasive assay produces diagnostic results that are superior to non-invasive/minimally-invasive techniques of the art, and approach results observed with the recognized standard invasive diagnostic procedure (colonoscopy). Moreover, a non-invasive assay utilizing more than one high-sensitivity/high-specificity technique results in diagnostic accuracy approaching 100%. As such methods of the invention provide a significant improvement in the ability to perform accurate non-invasive diagnosis of cancer.

What is claimed is:

1. A method of screening a human patient for cancer or precancer, the method comprising the steps of:
   (a) determining, in a patient sample of a bodily excretion or a bodily fluid, the amount of DNA greater than about 200 bp in length; and
   (b) comparing said amount to the amount of DNA greater than about 200 bp in length expected to be present in a sample obtained from a healthy patient,
      wherein a statistically significant larger amount of nucleic acids greater than about 200 bp in length in said patient sample indicates a positive screen.

2. The method of claim 1, further comprising the step of amplifying DNA in said sample of bodily excretion or bodily fluid using primers spaced about 200 bp apart.

3. The method of claim 1, further comprising the step of determining a ratio of said first amount of DNA to an amount of DNA having a length less than about 200 bp in said sample of bodily excretion or bodily fluid.

4. The method of claim 1, further comprising the step of:
   (c) selecting one or more informative nucleic acid mutations; and
   (d) performing an assay to detect the presence or absence of at least one of said mutations in said sample.

5. The method of claim 1, further comprising the step of determining an amount of amplifiable nucleic acid in said sample of bodily excretion or bodily fluid.

6. The method of claim 1, further comprising the step of detecting at least one nucleic acid mutation in said sample of bodily excretion or bodily fluid.

7. The method of claim 1, further comprising the step of performing a plurality of nucleic acid assays.

8. The method of claim 7, wherein said plurality comprises 2 to 5 assays.

9. The method of claim 7, wherein each assay detects a different nucleic acid marker.

10. The method of claim 7, wherein said assays are selected from the group consisting of multiple mutation detection, quantitative polymerase chain reaction, sequence-specific hybrid capture, oligo-ligation, amplification refractory mutation system, single-stranded conformational polymorphism detection, sequencing, mismatch detection, and single base extension.

11. The method of claim 1, further comprising the step of performing gel electrophoresis on nucleic acids obtained from said sample of bodily excretion or bodily fluid.

12. The method of claim 6, wherein said step of detecting at least one nucleic acid mutation further comprises performing a single base extension assay.

13. The method of any of claims 1, 2, or 6, wherein said method of screening provides a sensitivity of detection of at least 60% and a specificity of detection of at least 90%.

14. The method of claim 13, wherein said sensitivity and said specificity are determined by comparing results obtained in said screening method with results obtained using an invasive diagnostic method.

15. The method of claim 7, wherein at least one of said assays is an assay to detect loss of heterozygosity in at least a portion of a chromosomal arm.

16. The method of any of claims 1, 2, or 6, wherein said precancer is an adenoma.

17. The method of any of claims 1, 2, or 6, wherein said bodily excretion is selected from the group consisting of stool, and a homogenate of stool.

18. The method of any of claims 1, 2, or 6, wherein said bodily excretion or bodily fluid is selected from the group consisting of pus, sputum, urine, blood, cerebrospinal fluid, semen, and aspirate.

19. The method of claim 12, wherein said single base extension assay comprises the steps of:
   (a) annealing an oligonucleotide primer to a nucleic acid sample under conditions that promote exact complementary hybridization between said primer and a portion of a nucleic acid in said sample;
   (b) extending said primer by a single base;
   (c) separating said extended primer from said portion; and
   (d) identifying the base incorporated into said extended primer, hereby to identify said single base.

20. The method of claim 12, wherein said single base extension assay comprises the steps of:
   (a) annealing an oligonucleotide primer to a nucleic acid sample under conditions that promote exact complementary hybridization between said primer and a portion of a nucleic acid in said sample;
   (b) exposing said sample to two different deoxynucleotides under conditions to promote primer extension;
   (c) extending said primer until said primer can no longer be extended;
   (d) separating said extended primer from said portion; and
   (e) identifying the base incorporated into said extended primer, thereby to identify said single base.

21. The method of claim 20, wherein at least one of said deoxynucleotides is detectably labeled.

22. The method of claim 12, wherein said single base extension assay comprises identifying single nucleotides in each of a plurality of genomic loci.

23. The method of claim 22, wherein said genomic loci are selected from the group consisting of apc, Kras, p53, and bat-26.

24. The method of claim 7, wherein said plurality of assays comprises a quantitative polymerase chain reaction assay and an assay for a mutation in bat-26.

25. The method of claim 24, wherein said assay for a mutation in bat-26 comprises a primer extension assay to identify fragments of said bat-26.

26. The method of any of claims 1, 2, or 6, wherein said precancer is an adenoma.

27. The method of any of claims 1, 2, or 6, wherein said cancer is colorectal cancer.

28. The method of claim 13, wherein said sensitivity and said specificity are determined by comparing results obtained in said screening method with results obtained using an invasive diagnostic method.

29. The method of claim 28, wherein said invasive diagnostic method is a colonoscopy.

30. The method of claim 28, wherein said invasive diagnostic method is conducted contemporaneously with said screening method.

31. The method of claim 28, wherein said invasive diagnostic method is conducted within from about 3 hours to about 3 months of the time at which said screening method is conducted.

32. The method of claim 15, wherein said assay to detect loss of heterozygosity is selected from the group consisting of enumerative LOH and single base extension.

33. The method of claim 15, wherein said chromosomal arm is selected from the group consisting of chromosome 17p, chromosome 5p, chromosome 8p, chromosome 1q, and chromosome 18q.

* * * * *

SEQUENCE LISTING

<160> NUMBER OF SEQ ID NOS: 37

<210> SEQ ID NO 1
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: K-ras probe

<400> SEQUENCE: 1
gtggagtatt tgatagtgta ttaaccttat gtgtgac                37

<210> SEQ ID NO 2
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: apc probe apc-1309

<400> SEQUENCE: 2
ttccagcagt gtcacagcac cctagaacca aatccag                37

<210> SEQ ID NO 3
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: apc probe apc-1378

<400> SEQUENCE: 3
cagatagccc tggacaaaca atgccacgaa gcagaag                37

<210> SEQ ID NO 4
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: p53 probe

<400> SEQUENCE: 4
tactcccctg ccctcaacaa gatgttttgc caactgg                37

<210> SEQ ID NO 5
<211> LENGTH: 35
<212> TYPE: DNA
<213> ORGANISM: Homo sapiens
<220> FEATURE:
<221> NAME/KEY: misc_feature
<222> LOCATION: (1)..(35)
<223> OTHER INFORMATION: p53 probe

<400> SEQUENCE: 5
atttcttcca tactactacc catcgacctc tcatc                35

<210> SEQ ID NO 6
<211> LENGTH: 37
<212> TYPE: DNA
<213> ORGANISM: Homo sapiens

```
<220> FEATURE:
<221> NAME/KEY: misc_feature
<222> LOCATION: (1)..(37)
<223> OTHER INFORMATION: p53 probe

<400> SEQUENCE: 6
atgaggccag tgcgccttgg ggagacctgt ggcaagc                          37

<210> SEQ ID NO 7
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: p53 probe

<400> SEQUENCE: 7
gaaaggacaa gggtggttgg gagtagatgg agcctgg                          37

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence:PCR-A FOR
      (K-Ras)

<400> SEQUENCE: 8
gcggtcccaa aagggtcagt cctgctgaaa atgactgaa                        39

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:PCR-A-REV
      (K-Ras)

<400> SEQUENCE: 9
gcggtcccaa aagggtcagt catgaaaatg gtcagagaaa                       40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:PCR-B-FOR
      (APC-1309)

<400> SEQUENCE: 10
gcggtcgctt ttgggtcagt tgtagttcat tatcatcttt                       40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence:PCR-B-REV
      (APC-1309)

<400> SEQUENCE: 11
gcggtcgctt ttgggtcagt cttcgctcac aggatcttca                       40

<210> SEQ ID NO 12
<211> LENGTH: 39
<212> TYPE: DNA
```

```
<213> ORGANISM: Artificial Sequence
<220> FEATURE:
<223> OTHER INFORMATION: Description of Artificial Sequence:PCR-C-FOR
      (APC-1378)

<400> SEQUENCE: 12
gcggtcgcaa aagggacagt aggcacaaag ctgttgaat                              39

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:PCR-C-REV
      (APC-1378)

<400> SEQUENCE: 13
gcggtcgcaa aagggacagt tatcaagtga actgacagaa                             40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:PCR-D-FOR
      (APC-1450)

<400> SEQUENCE: 14
gcggtcccaa aagggtcagt cacctccacc acctcctcaa                             40

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:PCR-D-REV
      (APC-1450)

<400> SEQUENCE: 15
gcggtcccaa aagggtcagt gtatcagcat ctggaagaa                              39

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence:PCR-E-FOR
      (p53 Exon 5)

<400> SEQUENCE: 16
gcggtcccaa aagggtcagt ccatctacaa gcagtca                                37

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence:PCR-E-REV
      (p53 Exon 5)

<400> SEQUENCE: 17
gcggtcccaa aagggtcagt cagacctaag agcaatca                               38

<210> SEQ ID NO 18
<211> LENGTH: 38
<212> TYPE: DNA
<213> ORGANISM: Artificial Sequence
```

```
<220> FEATURE:
<223> OTHER INFORMATION: Description of Artificial Sequence:PCR-F-FOR
      (p53 Exon 7)

<400> SEQUENCE: 18
gcggtcccaa aagggtcaga taccaccatc cactacaa                               38

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence:PCR-F-REV
      (p53 Exon 7)

<400> SEQUENCE: 19
gcggtcccaa aagggtcaga gtatggaaga aatcggtaa                              39

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence:PCR-G-FOR
      (p53 Exon 8)

<400> SEQUENCE: 20
gcggtccctt ttgggtcact ctgcctcttg cttctctttt                             40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:PCR-G-REV
      (p53 Exon 8)

<400> SEQUENCE: 21
gcggtccctt ttgggtcact cttgtcctgc ttgcttacct                             40

<210> SEQ ID NO 22
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-A1

<400> SEQUENCE: 22
aacttgtggt agttggagct                                                   20

<210> SEQ ID NO 23
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-A2

<400> SEQUENCE: 23
acttgtggta gttggagctg                                                   20

<210> SEQ ID NO 24
<211> LENGTH: 20
<212> TYPE: DNA
```

-continued

```
<213> ORGANISM: Homo sapiens
<220> FEATURE:
<221> NAME/KEY: misc_feature
<222> LOCATION: (1)..(20)
<223> OTHER INFORMATION: SBE-A3

<400> SEQUENCE: 24
tgtggtagtt ggagctggtg                                               20

<210> SEQ ID NO 25
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: SBE-B1

<400> SEQUENCE: 25
aaatagcaga aataaaa                                                  17

<210> SEQ ID NO 26
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-C1

<400> SEQUENCE: 26
ctccctccaa aagtggtgct                                               20

<210> SEQ ID NO 27
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-C2

<400> SEQUENCE: 27
gtccacctgt acactatgtt                                               20

<210> SEQ ID NO 28
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-D1

<400> SEQUENCE: 28
ctcaaacagc acaaaccaag                                               20

<210> SEQ ID NO 29
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-E1

<400> SEQUENCE: 29
catgacggag gttgtgaggc                                               20
```

<210> SEQ ID NO 30
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-F1

<400> SEQUENCE: 30
gtaacagttc ctgcatgggc                                           20

<210> SEQ ID NO 31
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-F2

<400> SEQUENCE: 31
taacagttcc tgcatgggcg                                           20

<210> SEQ ID NO 32
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-F3

<400> SEQUENCE: 32
cctgcatggg cggcatgaac                                           20

<210> SEQ ID NO 33
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-F4

<400> SEQUENCE: 33
ctgcatgggc ggcatgaacc                                           20

<210> SEQ ID NO 34
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-G1

<400> SEQUENCE: 34
gacggaacag ctttgaggtg                                           20

<210> SEQ ID NO 35
<211> LENGTH: 20
<212> TYPE: DNA
<213> ORGANISM: Homo sapiens
<220> FEATURE:
<221> NAME/KEY: misc_feature
<222> LOCATION: (1)..(20)

```
<223> OTHER INFORMATION: SBE-G2

<400> SEQUENCE: 35
acggaacagc tttgaggtgc                                                20

<210> SEQ ID NO 36
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: SBE-G3

<400> SEQUENCE: 36
gtgcctatcc tgggagagac                                                20

<210> SEQ ID NO 37
<211> LENGTH: 314
<212> TYPE: DNA
<213> ORGANISM: Homo sapiens
<220> FEATURE:
<221> NAME/KEY: misc_feature
<222> LOCATION: (1)..(314)
<223> OTHER INFORMATION: BAT-26, wherein each "n" corresponds to a
      nucleotide of unknown identity

<400> SEQUENCE: 37
ccagtggtat agaaatcttc gatttttaaa ttcttaattt taggttgcag tttcatcact     60
gtctgcggta atcaagtttt tagaactctt atcagatgat tccaactttg gacagtttga   120
actgactact tttgacttca gccagtatat gaaattggat attgcagcag tcagagccct   180 taacctttt caggtaaaaa aaaaaaaaaa aaaaaaaaaa agggttaaaa atgttgattg    240
gttaannnnn nnngacagat agtgaagaag gcttagaaag gagctaaaag agttcgacat   300
caatattaga caag                                                    314
```